United States Patent

Naqui et al.

[11] Patent Number: 6,060,266
[45] Date of Patent: May 9, 2000

[54] SELF-CONTAINED INCUBATOR FOR GROWTH OF MICROORGANISM

[75] Inventors: Ali Naqui, Falmouth; Erwin F. Workman, Jr., Cape Elizabeth; Haoyi Gu, Portland; Mark W. Pierson, Saco, all of Me.

[73] Assignee: Idexx Laboratories, Inc., Westbrook, Me.

[21] Appl. No.: 09/043,960

[22] PCT Filed: Sep. 27, 1996

[86] PCT No.: PCT/US96/15525

§ 371 Date: Sep. 28, 1998

§ 102(e) Date: Sep. 28, 1998

[87] PCT Pub. No.: WO97/12029

PCT Pub. Date: Apr. 3, 1997

Related U.S. Application Data

[60] Provisional application No. 60/004,576, Sep. 29, 1995.

[51] Int. Cl.[7] ............................... C12Q 1/04; C12Q 1/02; C12N 1/12; G01N 33/53

[52] U.S. Cl. ........................... 435/34; 435/29; 435/252.1; 435/252.33; 435/252.8; 435/283.1; 435/848; 435/849; 435/975; 422/161; 422/56; 422/129; 422/138; 422/109; 422/108; 422/285

[58] Field of Search ........................... 435/43, 29, 252.1, 435/252.33, 252.8, 283.1, 848, 849, 975; 422/161, 56, 129, 138, 109, 108, 285

[56] References Cited

U.S. PATENT DOCUMENTS

| | | | |
|---|---|---|---|
| 3,960,670 | 6/1976 | Pflug | 435/34 |
| 4,458,674 | 7/1984 | Lemburg et al. | 128/1 B |
| 4,885,253 | 12/1989 | Kralovic | 435/34 |

OTHER PUBLICATIONS

Eastman et al., "Field incubator for measuring drug susceptibility of *Plasmodium falciparum*," *Journal of Tropical Medicine and Hygiene* 84:27–28 (1981).

Mealing et al., "An inexpensive portable incubator for tissue or cell cultures," *Brain Research Bulletin* 23:161–162 (1989).

*Primary Examiner*—Louise N. Leary
*Attorney, Agent, or Firm*—Lyon & Lyon LLP

[57] ABSTRACT

A self-contained incubator for growth of microorganism kit and methods for use of such a kit are provided. The kit and methods may detect the presence of microorganisms and may utilie a microorganism growth and indicator medium provided in a sample container along with a heat source, preferably generating heat through chemical means, and optionally heat shields, allowing for on-site testing of a microorganism present in a sample. The sample container may also include a removable vessel cap that includes a barrier separating the sample from a material capable of disinfecting the sample, thereby preventing contact of the sample and the material for a desired time period. The vessel cap may also be used independently in other applications.

41 Claims, 2 Drawing Sheets

SELF-CONTAINED INCUBATOR FOR GROWTH OF MICROORGANISM

Cross-Reference to Related Applications

This application is related to provisional application Ser. No. 60/004,576, filed Sept. 29, 1995, now abandoned which is incorporated herein by reference in its entirety, including any drawings and figures.

FIELD OF THE INVENTION

This invention relates generally to the fields of detecting and disposing of microorganisms. In particular, the invention relates to the use of incubators for detecting microorganisms and the use of storage containers for the disposal of the microorganisms.

BACKGROUND OF THE INVENTION

The following description of the background of the invention is provided to aid the reader in the understanding of the invention, but it is not admitted to constitute or describe prior art to the invention.

The collection of biological samples from the field, such as the sampling of water for microbiological contamination testing is an important aspect of maintaining the purity of water supplies.

Samples are often maintained under conditions which will allow for the later growth of any microorganisms present. However, little or no growth of any microorganisms in the sample occurs on site and during shipment of the sample to the testing laboratory. Growth based detection of any microorganism in the sample must await arrival at the testing facility, which delays the detection of the presence of microorganisms. Also, microbiological testing requires incubation of samples at elevated temperatures and such testing is usually done in a laboratory setting.

The use of portable incubation devices for the growth of biological samples, such as cells or tissues in culture is known. Such devices rely on the use of electrical elements such as batteries, heating coils and thermostats to maintain the proper temperature required for cellular growth. See, G. M. Eastham and K. H. Rieckmann, Journal of Tropical Medicine and Hygiene, 84:27–28 (1981) and, Geoffrey A. R. Mealing and Jean-Louis Scwhartz, Brain Research Bulletin, 23:161–162 (1989).

Lemberg et al. U.S. Pat. No. 4,458,674 disclose an infant incubator relying on convection flow from a heating element.

SUMMARY OF THE INVENTION

The present invention provides a portable incubation kit which relies on non-electromechanical devices in order to facilitate growth of a microorganism in a sample such that growth during shipment may occur. It also provides the option to conduct the microbiological testing on-site rather than shipping the sample to a laboratory. Surprisingly, the kit does not utilize any electrical components. The sample container and the vessel cap of the sample container, as described in detail below, provide a means for disinfecting a sample at a desired time and safely disposing the sample. By separating the sample from the disinfectant with a membrane or barrier, contact between the sample and the disinfectant can be prevented until the user breaks or removes the barrier or membrane and thereby allows contact and disinfection.

Thus, in one aspect the invention features a kit which advantageously provides for the incubation of a sample for on-site testing, which may contain a microorganism. It can also be used for concurrent shipment and incubation of a sample that may contain a microorganism. Instead of shipping the sample to a testing facility, the growth based detection of the organism can be conducted on-site, so that a signal generated by the growth of the organism may be rapidly detected by field personnel. If it is used as a shipping container, upon arrival at a testing facility, the growth of the organism(s) is complete or nearly complete and the result can be rapidly detected by facility personnel.

The kit includes a sample container for growth of a microorganism which may be present in a sample, and a heat pack. The kit is configured so that the heat pack is located to provide proper temperature for the growth of any such microorganism(s).

The "sample container" is generally any sterile vessel into which may be placed a sample which may contain a microorganism. The sample container may be made of plastic, glass or other nonporous substances which can contain a liquid or fluid without leaking. Such a sample container will allow growth of the microorganism to be detected and will generally contain from 10–100 ml liquid with appropriate space for gases as needed.

By "sample" is meant a fractional portion of a liquid to be tested, or if from a dry surface a transfer of some portion of material from the surface into the chamber. By "microorganism" is meant any one of a procaryotic, such as bacterial, or eucaryotic, such as molds, yeast, plant, animal and other eucaryotic organisms, all of which are too small to be easily seen with the naked eye.

By "heat pack" is meant a chemical heat source which may contain the following components: Iron particles, activated charcoal particles, cellulose, zeolite and moisture. Such packs are well known in the art, and are widely available. They are of the type used by, for example, skiers to warm their hands or feet. Any equivalent such heat packs are well known in the art and can be designed for use in this invention. Such packs are activated to generate heat without need for any special equipment. Generally, they can be activated by shaking after exposure of the pack to the air. In other embodiments, the heat pack may be a microwaveable gel able to maintain and dissipate heat over a several hour period. Such gels however do require some external source of heat energy for activation. Preferably, such a heat pack will maintain 10 or 100 mls of fluid in a chamber at above 30 degrees or 35 degrees C and below about 40 or 45 degrees C for about 20 to 30 hours when coupled with a proper insulating container.

In preferred embodiments, the kit also contains a heat shield located between the heat pack and the sample container; an insulating container which surrounds the sample container, the heat pack and if present the heat shield; and a microorganism growth and indicator medium which may be provided in the sample container (e.g., Colilert® medium for detection of coliforms and *Escherichia coli*, available from IDEXX Laboratories, Inc., Westbrook, Me.).

By "heat shield" is meant an element which may fit between the sample container and the heat pack to moderate the heat transfer between the heat pack and the sample container in order to provide proper sample temperature for the growth of targeted microorganism(s). The heat shield may be formed of, for example, cardboard, paper or perforated styrofoam or any other material suitable to moderate heat transfer.

By "insulating container" is meant a container which decreases the ability for heat to be transferred from or to the interior of the container. The insulating container may be formed of cardboard, or a material such as plastic surrounding a vacuum, for example a Thermos® type container. In a preferred embodiment the container is formed of polyfoam or Styrofoam™.

By "microorganism growth and indicator medium" is meant a medium which provides for the growth of specific target organisms but not others. For example, the presence of the specific bacterial, mold or yeast species may be made known by a signal generated on the basis of the cleavage of a nutrient-indicator releasing the indicator portion of the molecule by a specific enzyme, particular to a specific, bacterial, mold or yeast species. See Edberg, U.S. Pat. No. 5,429,933 (hereby incorporated by reference in its entirety, including any drawings and figures).

In preferred embodiments, the kit contains an observation window which allows comparison of a detectable signal generated by the growth of a microorganism with a standard which indicates the presence of a microorganism. The signal generating means may include a nutrient-indicator media, such as Colilert® nutrient-indicator media.

By "signal generated by the growth of a microorganism" is meant a detectable change in the contents of the sample container by, for example, human visual inspection or by detection in a device. Preferably, the signal comprises a change in the light emission or absorption characteristics of the contents of the sample in the sample container. Most preferably the alteration of the color of a signal is used. Signal generating means such nutrient-indicator media may also be used. Other signal detection systems may be employed. Examples of such signal detection systems include, but are not limited to, spectrophotometer, calorimeters, luminometers, fluorometers, and devices that measure the decay of radioisotopes. In a preferred embodiment, a dual color system is used for detection of coliforms and *Escherichia coli* in water samples. If coliform is present in a sample, the yellow color is generated due to ortho- nitrophenol (ONP) cleaved from nutrient indicator ortho- nitrophenol beta-D-galactopyranoside (ONPG) by β-D-glactosidase; the green color is generated in the sample due to cleavage of both nutrient indicators—ONPG and 5-bromo-4-chloro-3-indolyl beta-D-glucopyranoside(X-glcA)- are cleaved by β-D-galactosidase and β-D-glucuronidase from *E. coli*. The indicator portions of ONPG and X-glcA are yellow and blue respectively. When both color indicator are present in a sample, the sample appears to be green due to the mixture of yellow and blue colors.

In other aspects the invention features a method for use of the above kit. The method includes addition of sample to the sample container and activation of the heat pack. The heat pack is located near the sample container to heat the sample container and to maintain it at a temperature suitable for microorganism growth. If present, the heat shields can be placed appropriately to insure that proper temperature is maintained in the sample container. After a defined time, the results of the incubation can be scored by standard methods.

In another aspect the invention features a sample container capable of holding a sample that may contain a microorganism. The sample container may be used as a component of the kits described herein or independently of such kits. The sample container includes a sample vessel and a removable vessel cap. The vessel cap includes a barrier separating the sample from a material capable of disinfecting the sample, thereby preventing contact of the sample and the material for a desired time period. Thus, a user may remove the barrier at the desired time and bring the material in contact with the sample in order to disinfect the sample.

By "sample vessel" is meant any object having at least one opening that is capable of holding a sample added to the vessel through the opening. In preferred embodiments the sample vessel is generally cylindrical (although other shapes, such as rectangular, conical, spherical, as well as a wide variety of regular and irregular shapes, may be used) with an open end portion that has a first set of grooves and the vessel cap, defined below, contains a corresponding second set of grooves capable of interlocking with the first set and securing the vessel cap on the sample vessel. Of course, a wide variety of other means may also be used to secure the vessel cap to the sample vessel, including, among others, snap on lids By "vessel cap" is meant any object capable of attaching to the sample vessel to form a container dividing the contents of the container (e.g., the sample and air or another gas) from the exterior environment. The vessel cap may contain an aperature and the sample container may include a blister protruding through the aperature in the vessel cap. For example, the sample container may include a chlorine tablet in the blister, a membrane sealing the blister, and a washer. Thus, the vessel cap may contain a set of grooves so that the washer rests against the set of grooves, thereby holding the washer in place, thereby holding the membrane in place, thereby holding the chlorine tablet in place.

By "barrier" is meant any means of dividing the sample from the disinfectant material. Commonly, the barrier will be a sealable foil membrane that separates disinfectant material, such as a chlorine tablet, from the sample. Such a foil membrane may be opened simply by applying pressure through the chlorine tablet and thereby puncturing the membrane. Other barriers, such as sliding dividers or opening panels, could also easily be adapted to deliver the material to the sample or vice versa.

By "material capable of disinfecting the sample" is meant any substance that is capable of rendering safe a sample infected with a microorganism. The disinfectant preferably kills the microorganisms and thereby renders them incapable of causing infection. The material may be a chlorine tablet, for example a 100 mg rapid-release chlorine tablet.

In another aspect, the invention provides a removable vessel cap. The vessel cap may be used in conjunction with the sample container and/or kits described herein, or independently in other applications. The cap includes a material capable of disinfecting a sample and a barrier separating the material from the sample, thereby preventing contact of the material and the sample for a desired time period.

Other features and advantages of the invention will be apparent from the following description of the preferred embodiments thereof, and from the claims.

DETAILED DESCRIPTION OF THE INVENTION

The drawings will first briefly be described.
Drawings.

Kit

The kit of the present invention provides for the ability to conduct sampling for the presence of microorganisms. Generally, incubation times of 24 hours or less at temperatures between 30 degrees and 45 degrees Centigrade are provided for by the present invention. Other temperatures can be accommodated by use of more heat packs or by larger or smaller such packs.

Figure 1:
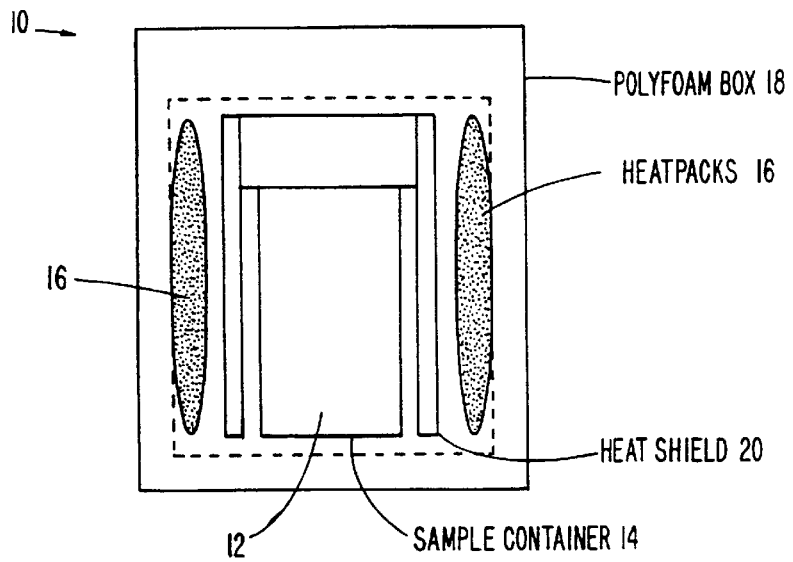
FIG. 1 is a longitudinal cross-sectional illustration of one embodiment of a kit of the present invention.

Referring to FIG. 1, in one preferred embodiment, kit 10 contains one Colilert® microorganism growth and indicator medium 12 (IDEXX Laboratories, Westbrook, Maine); these media are similar to those described by Edberg, supra, and allow rapid detection of the specified microbes in 24 hours after incubation at about 35 degrees C), one sterile 100 ml sample container 14, two commercially available heat packs 16 (Heat Pack™ available from Eastern Mountain Sports, which generates between 135 degrees F (58 degrees C) and 158 degrees F (70 degrees C) for up to eight hours without using insulating materials. The pack weighs about 20–30 grams and is formed from iron dust, activated charcoal powder, cellulose, zeolite and moisture), and one insulated container 18 which may be a polyfoam box (which snugly contains the heat packs and the chamber) with built in or separate heat shields 20 (cardboard having a thickness of about 0.2 mm). (The kit could include appropriate aperatures to act as an observation window and a built-in color comparator)

Use of the invention is simple and includes the steps of: (1) Adding a sample, which may be 100 ml, to sterile sample container 14, and adding the microorganism growth and indicator medium (in alternative embodiments the medium is prepackaged in the sterile sample container 14). Upon mixing of the sample with the nutrient-indicator media and subsequent incubation, if specific species of target bacteria are present a signal will be generated. More specifically, for the media needed above coliforms in the sample will produce a yellow color and *E. coli* will produce a green color. (2) Activating the heat packs. (3) Placing the sample container and heat packs in the insulating container. (4) The result can be scored after about 24 hours by visually inspecting the color of the sample. The order of the first three steps can be altered as recognized by those in the art.

Sample Container

Figure 5:
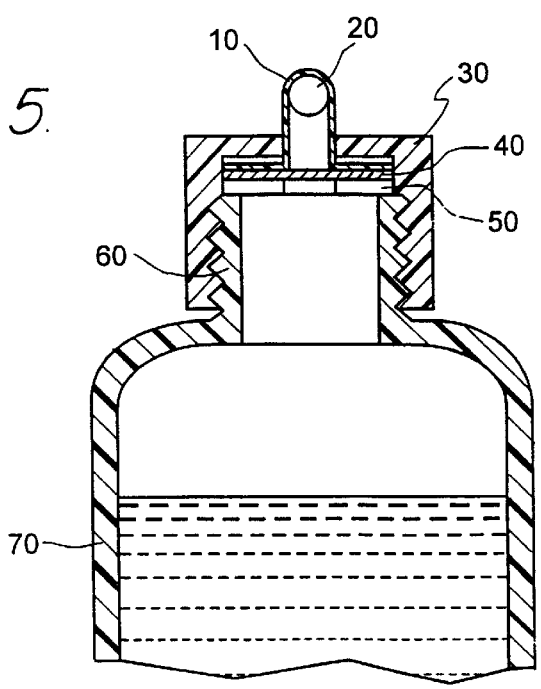
FIG. 5 illustrates a preferred embodiment of the sample container and vessel cap, including a chlorine tablet in a blister and separated from the sample by a barrier which is held in place by a washer resting against the grooves of the sample container.

FIG. 5 shows a preferred sample container of the present invention. The sample vessel 60 has an open end and holds a sample 70. The vessel cap 30 attaches to sample container 60. Disinfectant material 20, preferably a chlorine tablet, is held in a blister 10 protruding through the opening in vessel cap 30. Blister 10 preferably is a flexible dome shaped center piece forming a chamber and is sealed with moisture resistant membrane 40, which is held in place by washer 50. Washer 50 is held in place and rests against the grooves in sample vessel 60.

EXAMPLE 1

Validation of Kit

Table 1 illustrates the growth of various strains of *E. coli* in Colilert® reagent from various sources (the actual source is of no relevance to the experiment) at 35 degrees C in an air incubator for 24 hours versus the results obtained by incubation in the kit described above after 24 hours.

35° C. Incubator vs. Current Invention

| Bacterial strains | 35° C. Air Incubator at 24 hours | Current invention at 24 hours |
| --- | --- | --- |
| *Escherichia coli* ATCC 25922 (3.5 cfu/100 ml) | positive | positive |
| *Escherichia coli* EPA Q/C (6 cfu/100 ml) | positive | positive |
| *Escherichia coli* #3407A, Yale (4.4 cfu/100 ml) | positive | positive |
| *Escherichia coli* 19015 Yale (7 cfu/100 ml) | positive | positive |
| *Escherichia coli* #27 Yale (6.6 cfu/100 ml) | positive | positive |
| *Escherichia coli* ground turkey isolates (5.3 cfu/100 ml) | positive | positive |
| *Escherichia coli* Quanti-Cult (4.3 cfu/100 ml) | positive | positive |
| *Escherichia coli* English Q/C III-80B4 (3.6 cfu/100 ml) | positive | positive |
| Negative Control | negative | negative |

These data indicate that equivalent results to those obtained under standard conditions are obtained with a kit of this invention.

EXAMPLE 2

Temperature Ranges

Figure 2:
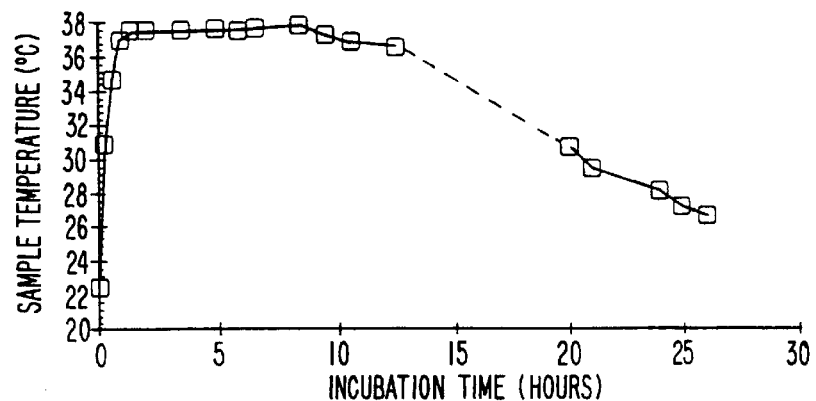
FIG. 2 illustrates the temperature range in a 10 ml sample heated by one heat pack over a 28 hour period.

As illustrated in FIG. 2, a graph of the temperature of a 10 ml sample plotted against hours after activation of one heat pack (in the kit described above) shows that the temperature did not rise above approximately 38 degrees centigrade and was maintained at 26 degree centigrade after 24 hours incubation. All temperature measurements were made with a thermocouple implanted in each sample, and readout was via a digital thermometer.

Figure 3:
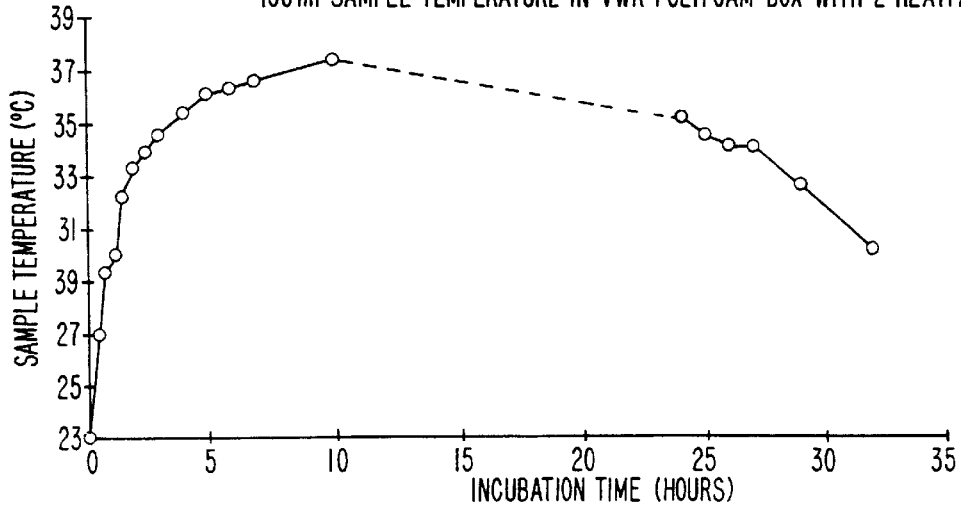
FIG. 3 illustrates the temperature range in a 100 ml sample heated by two heat packs placed in an insulating container over a 33 hour period.

A graph of the temperature of a 100 ml sample plotted against hours after activation of two heat packs (FIG. 3) shows that after 24 hours a temperature of approximately 35 degrees centigrade is still maintained, and the temperature did not rise above approximately 40 degrees centigrade.

EXAMPLE 3

Initial Sample Temperature at 4 Degrees C or Room Temperature

Figure 4:
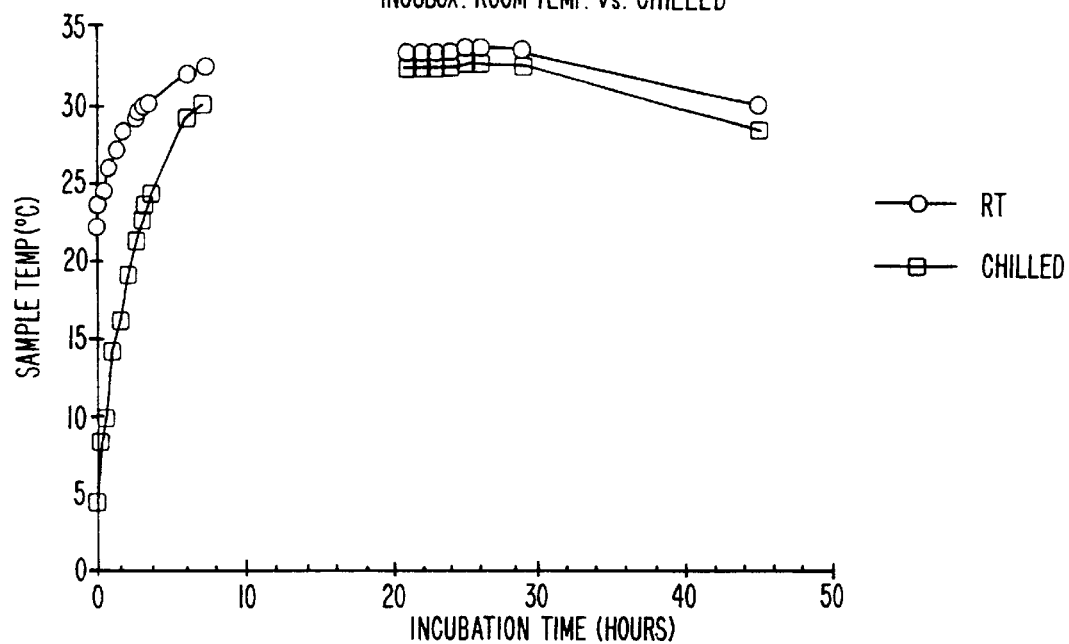
FIG. 4 illustrates the temperature range in a 100 ml sample initially at room temperature (about 23 degrees C) or initially at 4 degrees C heated by two heat packs placed in an insulated container over a 50 hour period.

As illustrated in FIG. 4, a graph of the temperature of a 100 ml sample plotted against hours after activation of the heat pack shows that whether the sample is initially at 4 degrees centigrade or at room temperature (about 23 degrees C) the sample heat profile over time is very similar, with only a 1 degree difference between the samples over most of the incubation period.

EXAMPLE 4

Colilert® Medium Test

Table 2 illustrates the testing of well water samples with Colilert® Media. The table illustrates that using Colilert®, incubation in both a 35 degree C air incubator and using the present kit resulted in negative results for all samples tested ("unspiked"). When 3.6 to 7.3 colony forming units (cfu) per 100 ml of *C. freundii* ATCC 8090 were added ("spiked") to the samples both incubation in both a 35 degree C air incubator and using the present kit resulted in positive results for all samples tested. All results are taken after 24 hours of incubation.

35° C. Air Incubator vs. Current Invention: Testing Well Water with Colilert®

|  | 35° C. Incubator | | Current invention | |
| --- | --- | --- | --- | --- |
| Sample | Unspiked | Spiked | Unspiked | Spiked |
| Site 1: raw | neg | pos | neg | pos |
| Site 1: filtered | neg | pos | neg | pos |
| Site 2: raw | neg | pos | neg | pos |
| Site 2: filtered | neg | pos | neg | pos |
| Site 3: filtered | neg | pos | neg | pos |
| Site 4: filtered | neg | pos | neg | pos |
| Site 5: filtered | neg | pos | neg | pos |
| Site 6: filtered | neg | pos | neg | pos |
| Site 7: raw | neg | pos | neg | pos |
| Negative control | neg | | neg | |

EXAMPLE 5

Operation of Sample Container and Vessel Cap Containing Chlorine Tablet

The following example describes a test of a vessel cap containing a chlorine tablet for use in the safe disposal samples which may contain harmful bacteria. As described above, the cap includes a dome shape flexible centerpiece with a breakable moisture resistant bottom layer forming a chamber to contain a chlorine tablet. Upon the completion of a test the user pushes the chlorine tablet downward to release it into the vessel containing the test sample. The rapid release chlorine tablet disinfects the test sample for safe disposal.

In the following example the cap was used with an IDEXX 100 ml Colilert® test vessel using Palintest® 100 mg rapid release chlorine tablet. Ten 100 ml positive Colilert® samples with approximately $10^6$ cfu per mililiter of *E. coli* ATCC#25922 were used to test the effectiveness of such chlorine tablet released from the prototype cap. The effectiveness of disinfection was checked by streaking samples onto blood agar plates in 1 minute intervals upon the releasing of the chlorine tablet. Blood agar plates were then incubated at 35° C. for 30 hours to observe the regrowth of bacteria.

The following table shows the test results

| | Time after chlorine tablet releasing | | | |
| --- | --- | --- | --- | --- |
| | 1 minute | 2 minutes | 3 minutes | 4 minutes |
| Bacteria re-growth | Yes | Yes | No | No |

The tests showed that samples were safe for disposal after 3 minutes of disinfection.

It will be readily apparent to one skilled in the art that various substitutions and modification may be made to the invention disclosed herein without departing from the scope and spirit of the invention.

All patents and publications mentioned in this specification are indicative of the levels of those skilled in the art to which the invention pertains. All such patents and publications are herein incorporated by reference to the same extent as if each individual publication was specifically and individually indicated to be incorporated by reference. One skilled in the art will readily appreciate that the present invention is well adapted to carry out the objects and obtain the ends and advantages mentioned, as well as those inherent therein. The methods, procedures, treatments, and devices described herein are presently representative of preferred embodiments, are exemplary and are not intended as limitations on the scope of the invention. Changes therein and other uses will occur to those skilled in the art which are encompassed within the spirit of the invention as defined by the scope of the claims.

What is claimed is:

1. A kit that can be used to detect a microorganism comprising:
   (a) a sample container capable of holding a sample that may include said microorganism,
   (b) a heat pack that can be activated to provide heat to said sample container,
   (c) at least one heat shield to be located between said sample container and said heat pack; and
   (d) an insulating container configured and arranged to hold said sample container and said heat pack sufficiently near one another to maintain a proper incubation temperature within said sample container,
   wherein said sample container is configured and arranged to provide a proper incubation temperature for growth of said microorganism.

2. The kit of claim 1, wherein said kit further comprises an indicator growth medium.

3. The kit of claim 2, wherein said indicator growth medium is a solid.

4. The kit of claim 2, wherein said indicator growth medium is a liquid.

5. The kit of claim 2, wherein said kit further comprises a window to allow observation of said sample container.

6. The kit of claim 1, wherein said kit comprises more than one sample container.

7. The kit of claim 1, wherein said kit comprises more than one heat pack.

8. The kit of claim 2, wherein said kit comprises more than one indicator growth medium.

9. The kit of claim 1, wherein said microorganism is a procaryotic organism.

10. The kit claim 1 of, wherein said microorganism is a eucaryotic organism.

11. The kit of claim 1, wherein said microorganism is a coliform.

12. The kit of claim 1, wherein said microorganism is an *Escherichia coli*.

13. The kit of claim 1, wherein said sample container is plastic.

14. The kit of claim 1, wherein said sample container has a volume between 10 mL and 250 mL.

15. The kit of claim 1, wherein said sample container has a volume between 80 mL and 130 mL.

16. The kit of claim 1, wherein said sample container comprises a sample vessel and a vessel cap which contains an aperture and which further comprises a blister protruding through the aperature in said vessel cap.

17. The kit of claim 16, wherein said sample vessel is generally cylindrical with an end portion that has a first set of grooves and wherein said vessel cap contains a corresponding second set of grooves capable of interlocking with said first set and securing said vessel cap on said sample vessel.

18. The kit of claim 16, wherein said vessel cap includes a material capable of disinfecting said sample container in said blister.

19. The kit of claim 18, wherein said material is a chlorine tablet.

20. The kit of claim 19, wherein said chlorine tablet is a 100 mg rapid-release chlorine tablet.

21. The kit of claim 19, wherein said sample container further comprises a membrane sealing said blister, and a washer.

22. The kit of claim 21, wherein said vessel cap contains a set of grooves and said washer rests against said set of grooves, thereby holding said membrane in place, thereby holding said chlorine tablet in place.

23. The kit of claim 1, wherein said heat pack is adapted to maintain 10 mls of liquid in said sample container at an average temperature of about 30° C. during a 26 hour incubation period when the temperature outside said insulating container is about 23° C.

24. The kit of claim 1, wherein said heat pack is adapted to maintain 10 mls of liquid in said sample container at an average temperature of about 37° during a 10 hour incubation period when the temperature outside of said insulating container is about 23° C.

25. The kit of claim 1, wherein said heat pack is adapted to maintain 10 mls of liquid in said sample container at an average temperature of about 37° during a 5 hour incubation period when the temperature outside of said insulating container is about 23° C.

26. The kit of claim 1, wherein said heat pack is adapted to maintain 100 mls of liquid in said sample container at an average temperature of about 30° C. during a 15 hour incubation period when the temperature outside of said insulating chamber is about 23° C.

27. The kit of claim 1, wherein said heat pack is adapted to maintain 100 mls of liquid in said sample container at an average temperature of about 37° C. during a 10 hour incubation period when the temperature outside of said insulating chamber is about 23° C.

28. The kit of claim 1, wherein said heat pack is adapted to maintain 100 mls of liquid in said sample container at an average temperature of about 37° C. during a 5 hour incubation period when the temperature outside of said insulating chamber is about 23° C.

29. A method of detecting the presence of a microorganism in a sample comprising the steps of:
   (a) providing a kit comprising a sample container capable of holding a sample that may include said microorganism, a heat pack that can be activated to provide heat to said sample container at least one heat shield to be located between said sample container and said heat pack, and an insulating container configured and arranged to hold said sample container and said heat pack sufficiently near one another to maintain a proper incubation temperature within said sample container, wherein said sample container is configured and arranged to provide a proper incubation temperature for growth of said microorganism;
   (b) depositing said sample in said sample container for growth of said microorganism;
   (c) activating said heat pack to supply heat to said sample container; and
   (d) placing the sample container and heat pack in the insulated container and positioning said heat pack and heat shield to provide heat to said sample container, wherein said steps (b), (c), and (d) may be performed in any order.

30. The method of claim 29, further comprising the step or adding a microorganism growth and indicator medium to said sample container.

31. A sample container capable of holding a sample that may contain a microorganism comprising a sample vessel and a removable vessel cap, wherein said vessel cap contains an aperture and a blister protruding through the aperture the blister containing a material capable of disinfecting said sample and further includes a barrier separating said sample from said material thereby preventing contact of said sample and said material for a desired time period.

32. The sample container of claim 31, wherein said sample vessel is generally cylindrical with an end portion that has a first set of grooves and wherein said vessel cap contains a corresponding second set of grooves capable of interlocking with said first set and securing said vessel cap on said sample vessel.

33. The sample container of claim 31, wherein said material is a chlorine tablet.

34. The sample container of claim 33, wherein said chlorine tablet is a 100 mg rapid-release chlorine tablet.

35. The sample container of claim 33, wherein said sample container further comprises a membrane sealing said blister, and a washer.

36. The sample container of claim 35, wherein said vessel cap contains a set of grooves and said washer rests against said set of grooves, thereby holding said washer in place, thereby holding said membrane in place, thereby holding said chlorine tablet in place.

37. A removable vessel cap having an aperture and a blister that protrudes through the aperature in said vessel cap, a material capable of disinfecting a sample and a barrier separating said material from said sample, thereby preventing contact of said material and said sample for a desired time period.

38. The vessel cap of claim 37, wherein said vessel cap contains a first set of grooves capable of interlocking with a second set of grooves on a sample vessel and securing said vessel cap on said sample vessel.

39. The vessel cap of claim 37, wherein material is a chlorine tablet.

40. The vessel cap of claim 39, wherein said chlorine tablet is a 100 mg rapid-release chlorine tablet.

41. The vessel cap of claim 37, wherein a chlorine tablet is sealed in the blister by a membrane sealing said blister, and a washer and wherein said vessel cap contains a set of grooves and said washer rests against said set of grooves, thereby holding said washer in place, thereby holding said membrane in place, thereby holding said chlorine tablet in place.

* * * * *